(12) United States Patent
Zhao et al.

(10) Patent No.: US 6,686,466 B2
(45) Date of Patent: Feb. 3, 2004

(54) PHOTOCHROMIC OXAZINE COMPOUNDS AND METHODS FOR THEIR MANUFACTURE

(75) Inventors: Weili Zhao, Zurich (CH); Erick M. Carreira, Zumikon (CH)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 7 days.

(21) Appl. No.: 10/008,787

(22) Filed: Nov. 13, 2001

(65) Prior Publication Data

US 2003/0125552 A1 Jul. 3, 2003

(51) Int. Cl.$^7$ .................. C07D 295/00; C07D 265/00
(52) U.S. Cl. ..................... 544/70; 544/71; 544/99; 546/64
(58) Field of Search ....................... 546/64; 544/70, 544/71, 99

(56) References Cited

U.S. PATENT DOCUMENTS

| | | |
|---|---|---|
| 3,562,172 A | 2/1971 | Ono et al. |
| 4,634,767 A | 1/1987 | Hoelscher et al. |
| 4,637,698 A | 1/1987 | Kwak et al. |
| 4,699,473 A | 10/1987 | Chu |
| 4,949,471 A | 8/1990 | Garcia Pastor et al. |
| 5,017,698 A | 5/1991 | Machida et al. |
| 5,801,243 A | 9/1998 | Melzig et al. |
| 5,905,148 A | 5/1999 | Krongauz et al. |
| 6,004,486 A | 12/1999 | Chan |
| 6,019,914 A | 2/2000 | Lokshin et al. |

FOREIGN PATENT DOCUMENTS

| | | |
|---|---|---|
| DD | 153 690 A | 1/1982 |
| DD | 156 372 A | 8/1982 |
| GB | 2 338 955 A | 1/2000 |
| JP | 04 091082 A | 3/1992 |

OTHER PUBLICATIONS

Nicolaides, Demetrios N. et al., Reactions of 2–(methoxyimino) benzen–1–ones with α–alkylethoxycarbonylmethylene (triphenyl) phosphoranes, Tetrahedron, Elsevier Science Publishers, Amsterdam, NL, Nol. 57, No. 46, pp. 9469–9474, Nov. 12, 2001.

Ulrich Grummt et al., "New Photochromic 2H–1,4–Oxazines and Spiro–2H–1,4–Oxazines", Tetrahedron, 1981, 3945–3948, vol. 22, No. 40.

PCT Int'l. Search Report, dated May 25, 2003, for PCT Int'l. Appln. No. PCT/US02/35571.

*Primary Examiner*—Amelia Owens
(74) *Attorney, Agent, or Firm*—Lois Gianneschi

(57) ABSTRACT

The present invention provides photochromic oxazine compounds and methods for their manufacture, which compounds are useful as photochromic compounds. The compounds of the invention have aromatic substituents on the 2 position of the oxazine moiety.

11 Claims, No Drawings ered by Formula VI may be prepared by alternative reactions as shown in
PHOTOCHROMIC OXAZINE COMPOUNDS AND METHODS FOR THEIR MANUFACTURE

FIELD OF THE INVENTION

The present invention relates to oxazine compounds. In particular, the invention provides oxazine compounds and methods for their manufacture, which compounds are useful as photochromic compounds.

BACKGROUND OF THE INVENTION

Various classes of photochromic compounds have been synthesized and suggested for use in applications in which reversible color changes or darkening is induced by sunlight. For example, spirooxazine and chromene compounds are known for excellent fatigue resistance. Additionally, photochromic 2,2-disubstituted [2H-1,4]-naphthoxazine compounds, such as those are disclosed in U.S. Pat. No. 5,801,243, are known. These compounds have better fatigue resistance than chromene compounds, but are disadvantageous in that methods for their preparation are extremely limited. Thus, a need exists for additional photochromic oxazine compounds that overcome the disadvantages of the known compounds.

DESCRIPTION OF THE INVENTION AND ITS PREFERRED EMBODIMENTS

The present invention provides oxazine compounds having an aromatic substituent at the 2 position of the oxazine moiety, as well as methods for synthesizing these compounds.

In one embodiment, the invention provides a compound comprising, consisting essentially of, and consisting of Formula I:

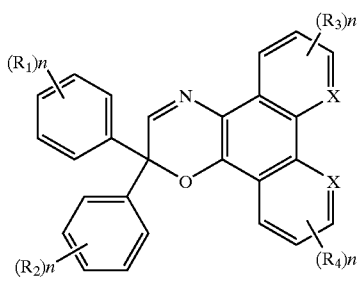

I wherein X is nitrogen or carbon; $R_1$, $R_2$, $R_3$, and $R_4$ are identical or different and each independently may be hydrogen, hydroxy, halogen, benzyl, formyl, trifluoromethyl, nitro, cyano, aryl, aryl ($C_1$–$C_4$)alkyl, aryloxy, cyclo ($C_3$–$C_6$)alkyl, ($C_1$–$C_{18}$)alkoxy, halo ($C_1$–$C_6$) alkoxy, ($C_1$–$C_4$)alkoxycarbonyl or a heterocyclic nitrogen-containing substituent having 5 or 6 atoms in the ring, such as, without limitation, pyrrolidino, piperidino and morpholino; and n=1 or 2. When n=1, there is one substituent on the phenyl moiety or pyridine moiety and $R_1$ or $R_2$ may be located at the ortho, meta, or para position of the phenyl ring.

In a preferred embodiment, X is carbon or nitrogen; $R_1$, $R_2$, $R_3$, and $R_4$ are each independently hydrogen, hydroxy, fluoro, chloro, bromo, benzyl, formyl, trifluoromethyl, nitro, cyano, aryl, aryl ($C_1$–$C_4$)alkyl, aryloxy, cyclo ($C_3$–$C_6$)alkyl, ($C_1$–$C_4$)alkoxy, ($C_1$–$C_4$)alkoxycarbonyl, or a heterocyclic nitrogen-containing substituent having 5 or 6 atoms in the ring, such as without limitation pyrrolidino, piperidine, and morpholino; and n=1 or 2. More preferably, X is carbon or nitrogen, $R_1$, $R_2$, $R_3$, and $R_4$ are each hydrogen, fluoro, chloro, methyl, methoxy, ethoxy, methoxycarbonyl, ethoxycarbonyl, piperidino, morpholino, or pyrrolidino, and n=1 or 2.

In a more preferred embodiment the invention provides a compound that is 2,2-diphenyl-phenanthro (9,10)-2H-[1,4]-oxazine, 2-(4-methoxyphenyl)-2-phenyl-phenanthro (9,10)-2H-[1,4]-oxazine, 2-(4-fluorophenyl)-2-(4-methoxyphenyl)-phenanthro (9,10)-2H-[1,4]-oxazine, or 2,2-Bis(4-methoxyphenyl)-phenanthro (9,10)-2H-[1,4]-oxazine.

The compound of Formula I may be prepared by the following Reactions A through E. For all reactions, $R_1$, $R_2$ and "n" are the same as defined hereinabove. Benzophenones represented by Formula IV below are commercially available or may be prepared by Friedel-Crafts reaction using a benzoyl chloride of Formula II and a benzene of Formula III. The Friedel-Crafts reaction is described in George A, Olah, "*Friedel-Crafts and Related Reactions*" (Vol. 3, 1964).

In Reaction A, the compounds represented by Formulae II and III are dissolved in dichloromethane and reacted in the presence of a Lewis acid including, without limitation, aluminum chloride, to form the corresponding substituted benzophenone.

Reaction A

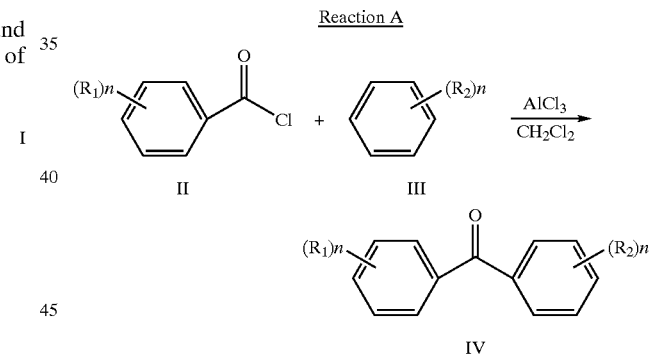

The disubstituted acrylic acid represented by Formula VI may be prepared by alternative reactions as shown in Reaction B and C. In reaction B, the benzophenone is reacted with acetonitrile in the presence of an excess amount of sodium hydroxide to form the 2,2-disubstituted acrylonitrile of Formula V, which process is described in J. Org. Chem., 44 (25), 4640–4649 (1979). After hydrolyzation with sodium hydroxide in ethylene glycol, followed by acidification, the disubstituted acrylic acid may be obtained.

Alternatively in Reaction C, a Hornor-Emmons reaction as described in Tetrahedron, 52 (31), 10455–10472 (1996), may be conducted starting from a benzophenone. The resulted 3,3-disubstituted acrylic acid ethyl ester of Formula VII may be hydrolyzed to form the disubstituted acrylic acid represented of Formula VI. $R_1$, $R_2$ and "n" are the same as defined herein before.

Reaction B

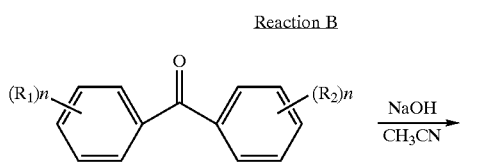

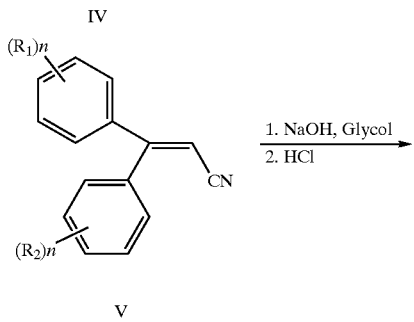

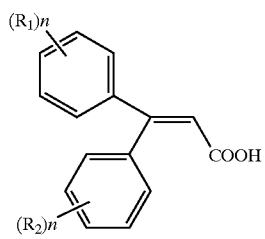

Reaction C

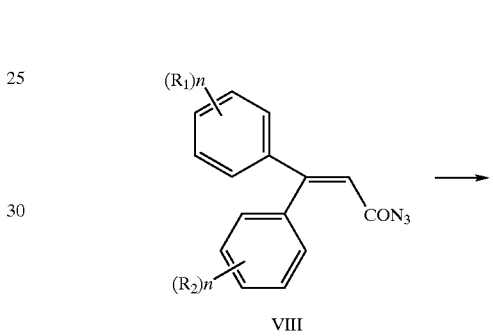

In Reaction D, the 3,3-di-substituted acrylic acid is treated with thionyl chloride, followed by reaction with sodium azide to form the 3,3-disubstituted but-2-enoyl azide of Formula VIII. Under heating in nonpolar solvent including, without limitation, benzene or toluene, the 3,3-disubstituted but-2-enoyl azide rearranges to form the isocyanate of Formula IX.

Reaction D

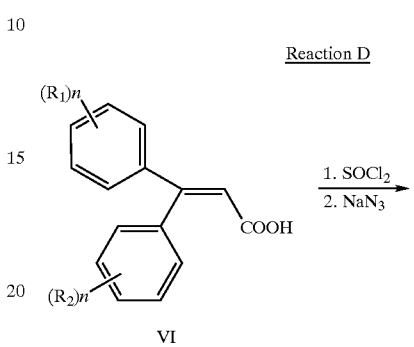

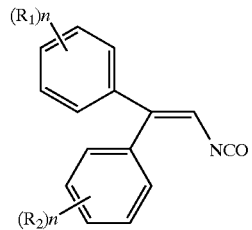

The critical step in the synthesis of the photochromic oxazines of Formula I is shown in Reaction E, in which an isocyanate derivative of Formula IX is reacted with a symmetric quinone including, without limitation, a substituted or unsubstituted phenanthrene-9,10-dione and substituted or unsubstituted 1,10-phenanthroline-5,6-dione of Formula X, in the presence of a catalytic amount of triphenyl arsen oxide in a suitable organic solvent under mild conditions for a time, generally about 2 to about 10 hours, sufficient to complete the reaction. Organic solvents that may be used include, without limitation, benzene, dioxane, tetrahydofuran ("THF"), toluene, and the like and combinations thereof Reaction temperatures will vary and typically range from about 40° C. to about 120° C. In a preferred embodiment, a solvent such as benzene or toluene is used and the reaction is carried out at about 50 to about 110° C. for about 1 to about 15 hours. More preferably, the solvent is toluene or benzene and the reaction is carried out at about 60 to about 80° C. for about 2 to about 4 hours.

Reaction E

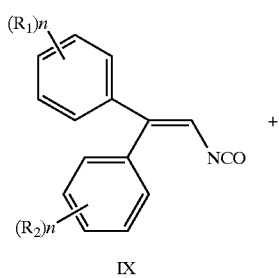

+

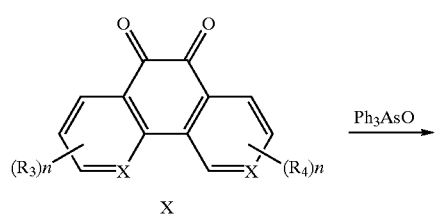

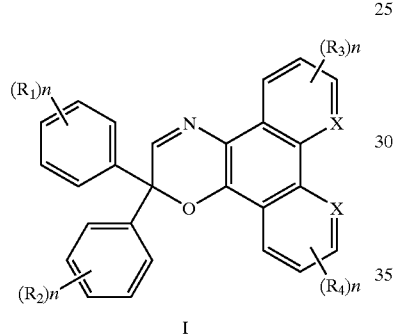

Reaction F

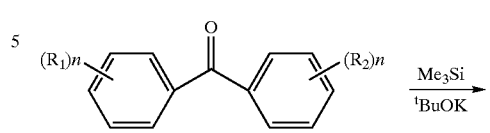

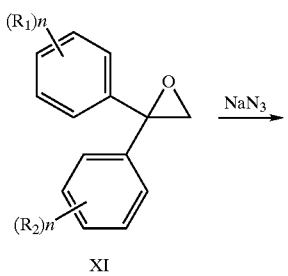

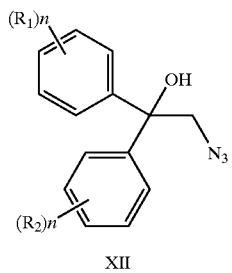

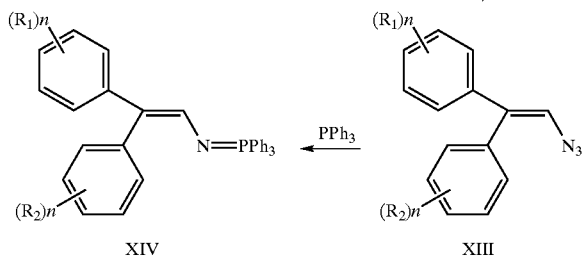

Alternatively, the photochromic oxazine compounds of the invention may be prepared as shown in Reactions F and G. In the reactions $R_1$, $R_2$ and "n" are the same as defined hereinabove. In Reaction F, the benzophenone of Formula IV is converted to a 1,1-disubstituted epoxide of Formula XI by treatment with trimethyl sulfoxinium iodide and potassium tert-butoxide in dimethyl sulfoxide ("DMSO"). This reaction is described in J. Org. Chem., 62 (19), 6547–6561 (1997). Treatment of the substituted epoxide with sodium azide in N, N-dimethylformamide ("DMF") * in the presence of lithium chloride forms the substituted 2-azido-1,1-disubstituted ethylene of Formula XII.

Following the procedure described in J. Org. Chem., 33 (6), 2411–2416 (1968), dehydration of the 2-azido-1,1-disubstituted ethylene by treatment with thionyl chloride in pyridine results in the 2-azido-1,1-disubstituted ethylene of Formula XIII. A subsequent Staudinger reaction by treatment of the 2-azido-1,1-disubstituted ethylene with triphenylphosphine forms the ylide represented by Formula XIV.

Heating the ylide with a symmetric quinone of Formula X in any suitable solvent for a time sufficient to complete the reaction affords the desired oxazine of Formula I. The organic solvent used may be, without limitation, benzene, dioxane, tetrahydofuran, toluene, and the like and combinations thereof. Reaction temperature will vary and typically ranges from about 60° C. to about 120° C. and reaction time from about 2 to about 24 hours. In a preferred embodiment, the solvent used is benzene or toluene and the reaction is carried out at about 70 to about 100° C. for about 5 to about 5 hours.

Reaction G

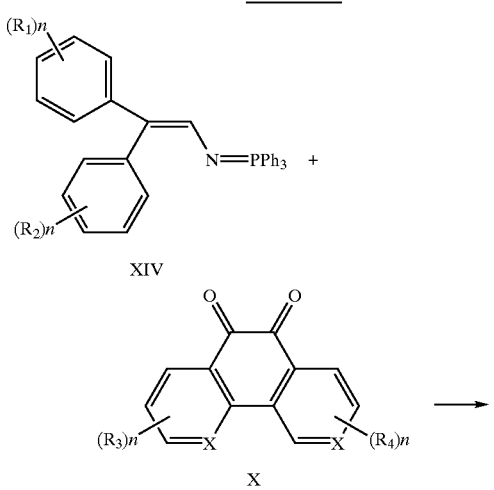

-continued

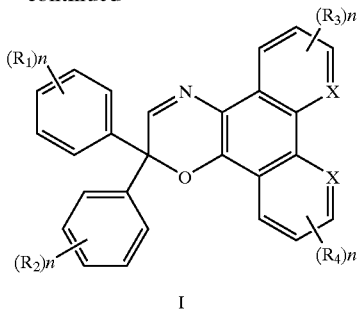

I

The oxazines of the invention may be used in any applications in which organic photochromic substances are typically employed including, without limitation, ophthalmic lenses, windows, automotive transparencies, polymer films, and the like. The oxazines of the invention may be utilized in an organic solvent or in organic polymer host. The organic solvent may be any suitable solvent including, without limitation, benzene, toluene, methyl ethylketone, acetone, ethanol, methanol, tetrahydrofuran, dioxane, ethyl acetate, ethylene glycol, xylene, cylcohexane, N-methyl pyrrolidinone, and the like and combinations thereof The host polymer maybe a transparent polymer such as polymethacrylate, polystyrene, polycarbonate and cellulose acetate. The amount of oxazine used is such that the organic host material to which the photochromic compound, or mixture of compounds, is applied or in which they are incorporated exhibits the desired resultant color, e,g., a substantially neutral color when activated with unfiltered sunlight. The amount of photochrome used in the solution or polymer matrix depends on the degree of darkening desired and usually is about 0.001 to about 20% by weight of the host polymer.

The invention will be clarified further by a consideration of the following, non-limiting examples.

EXAMPLES

Example 1

Step 1.

Into a 100 ml three-necked flask was charged solid KOH (3.30 g, 0.05 mole) and 25 ml acetonitrile under argon which was then heated to reflux. Benzophenone (9.1 g, 0.05 mole) in 20 ml acetonitrile was added in a stream with stirring. After 8 hours of reflux, the hot reaction solution was poured onto 100 g crushed ice and extracted with dichloromethane (3×15 ml). The combined organic extract was washed with water, dried over anhydrous sodium sulfate, and filtered. Solvent was removed, the residue was purified by flash chromatography on silica gel (ether-hexane 1:5 as eluent), 7.9 g colorless oil was obtained (yield: 77%). $^1$HNMR showed the product to have a structure consistent with 3,3-diphenyl-acrylonitrile.

$^1$HNMR (CDCl$_3$): δ5.75 (s, 1H), 7.27–7.50 (m, 10H).

Step 2.

The 3,3-diphenyl-acrylonitrile (5.76 g, 2.81 mmol) produced in Step 1 and sodium hydroxide (11.2 g, 280 mmol) were refluxed in a mixture of 180 ml ethylene glycol and 1 ml water for 3 days. The reaction mixture was cooled down and diluted with 100 ml water, acidified with 5 M hydrochloric acid until the pH was <1, filtered with suction and washed with water completely. The solid paste was dissolved in ethyl acetate, and washed with dilute hydrochloric acid. The organic layer was separated and the aqueous layer was extracted twice with ethyl acetate. The combined ethyl acetate solution was dried over anhydrous sodium sulfate, and filtered. The solvent was removed in vacuo until the total volume was about 40 ml. The solution was filtered through a short silica gel column and washed with ethyl acetate. After removal of the solvent in vacuo, the residue was titrated with a small volume of hexane-ethyl acetate (4:1), recrystallized from ethyl acetate/hexane. Colorless crystal (5.34 g) was obtained (yield: 84.8%). $^1$HNMR showed that the product to have a structure consistent with 3,3-diphenyl-acrylic acid.

$^1$HNMR (CDCl$_3$): δ6.38 (s, 1H), 7.24–7.35 (m, 1H), 7.40–7.46 (m, 3H).

Step 3.

A suspension of acrylic acid (225 mg, 1 mmol) in dry benzene (4 ml) was refluxed with excess thionyl chloride (0.20 ml) for two hours. Removal of the solvent and excess thionyl chloride under reduced pressure gave the required 3,3-diphenyl-acrylic acid chloride. The acyl chloride in dry THF (2.5 ml) was cooled to 0° C. and treated with a solution of sodium azide (130 mg, 2 mmol) in water (2 ml). The mixture was stirred at 0° C. for 2 hours before water (10 ml) was added. The mixture was extracted with ether (2×10 ml), and dried with anhydrous sodium sulfate.

Removal of the solvent under reduce pressure afforded a yellow oil (200 mg) which was heated to 80° C. overnight together with 9,10-phenanthrene quinone (146 mg, 0.7 mmol) and triphenyl arsen oxide (16 mg) in dry toluene (12 ml). After chromatography (silica gel, dichloromethane-hexane 2:1 as eluent) and recrystallization from dichloromethane-hexane, 203 mg of the desired photochromic oxazine was obtained as white (slightly pale yellow) crystal (yield: 52.7%).

Example 2

Step 1.

Trimethylsulfoxonium iodide (1.12 g, 5 mmol) and potassium tert-butoxide (0.59 g, 5 mmol) were stirred in DMSO (10 ml) at room temperature for 10 minutes. Benzophenone (0.77 g, 4.2 mmol) was added and the mixture stirred at 40° C. for 24 hours after which it was cooled, crushed ice and water were added and extracted with ether (3×15 ml). The combined etherate solution was washed with water, dried over anhydrous magnesium sulfate and filtered. Solvent was removed and a pale yellow oil resulted that contained mostly 1,1-diphenyloxirane, which was used directly in Step 2 without purification.

$^1$HNMR (CDCl$_3$): δ3.29 (s, 2H), 7.30–7.40 (m, 10H).

Step 2.

The oil obtained in Step 1 along with sodium azide (0.36 g, 5.5 mmol) and lithium chloride (0.32 g, 7.5 mmol) in DMF (20 ml) were stirred at 80° C. under nitrogen for 24 hours, cooled, water (20 ml) was added, and the mixture was extracted with ether (3×20 ml). The combined etherate solution was washed with water, dried over anhydrous magnesium sulfate and filtered. After removal of the solvent in vacuo, the residue was purified by chromatography on silica gel (dichloromethane-hexane 1:2 as eluent). A colorless oil (0.64 g) was obtained. Infrared spectra showed a strong absorption at 2100 cm$^{-1}$.

$^1$HNMR (CDCl$_3$): δ2.91 (s, 2H), 4.02 (s, 2H), 7.27–7.45 (m, 10 H).

$^{13}$CNMR (CDCl$_3$): $^1$HNMR (CDCl$_3$): δ60.4, 78.2, 126.3, 127.8, 128.5, 143.8.

Step 3.

The 2-azido-1,1-diphenylmethanol obtained in Step 2 (160 mg, 0.67 mmol), thionyl chloride (0.2 ml) and pyridine (2 ml) were refluxed for 2 hours. After being cooled, water (10 ml) was added carefully into the reaction mixture under ice-water cooling, and extracted with ether (3×5 ml). The combined etherate solution was washed with 4 M hydrochloric acid, water and brine, dried over anhydrous magnesium sulfate, and filtered. After removal of the solvent, a yellow oil (120 mg) was obtained. Infrared spectra showed strong absorption at 2097 cm$^{-1}$. $^1$HNMR showed that the resulted product was pretty pure 2-azido-1,1-diphenyl ethylene.

$^1$HNMR (CDCl$_3$): δ6.69 (s, 1H), 7.18–7.42 (m, 10H).

Step 4.

To the 2-azido-1,1-diphenyl ethylene prepared in Step 3 in dry toluene (5 ml) was added triphenylphosphine (157 mg, 0.6 mmol) at room temperature under nitrogen. After 0.5 hour stirring, 9,10-phenanthrene-9,10-dione (104 mg, 0.5 mmol) was added. The mixture was heated at 80° C. overnight. Photochromic product was obtained by chromatography on silica gel (dichloromethane-hexane 1:1 as eluent) and re-crystallized from dichloromethane/hexane, as pale yellow crystal (45 mg).

$^1$HNMR (CDCl$_3$): δ7.24–7.29 (m, 6H), 7.46–7.70 (m, 8H), 8.12 (s, 1H), 8.43–8.52 (m, 1H), 8.53–8.62 (m, 3H).

$^{13}$CNMR (CDCl$_3$): δ79.5, 122.5, 122.7, 122.8, 123.0, 125.1, 126.9, 126.9, 127.1, 127.3, 127.6, 128.4, 128.6, 129.8, 131.3, 128.0, 141.4, 155.7.

Example 3

Step 1.

To a stirred suspension of sodium hydride (95%, 0.507 g, 20 mmol) in THF (15 ml) was added 2–3 ml a solution of triethylphosphono acetate (4.48 g, 20 mmol) in THF (20 ml). A tiny drop of ethanol was added to initialize the reaction, then the rest of the triethylphosphono acetate solution was added dropwise under ice-water cooling over 40 minutes. After 15 minutes of stirring, the reaction mixture was transferred into a dropping funnel and added dropwise to a boiling solution of 4-methoxybenzophenone (4.38 g, 20 mmol) in THF (20 ml). After 24 hours reflux, most of the solvent was removed. To the cooled residue was added a saturated solution of aqueous sodium chloride (20 ml) and extracted with dichloromethane. Removal of dichloromethane gave a pale yellow oil (5.42 g) containing mostly (E) and (Z)-3-p-methoxyphenyl-3-phenyl-acrylic acid ethyl ester as characterized by $^1$HNMR and which was used directly in Step 2 without further purification.

Step 2.

The oil obtained in Step 1 was hydrolyzed in a solution of KOH (5.07 g, methanol (30 ml)) under reflux for 1 hour. The cooled reaction mixture was poured into ice-water, acidified with dilute hydrochloric acid until the pH was <1 and extracted with ethyl acetate (3×20 ml). The combined organic solution was dried over anhydrous sodium sulfate, the solvent was removed, the residue was re-crystallized from ethyl acetate/hexane and a white solid was obtained. The mother liquid was subjected to chromatography and re-crystallization. A total of 3.826 g desired product was obtained as white solid and 0.677 g unreacted ketone was recovered (yield: 75.3%). $^1$HNMR showed that the recovered product to be a mixture of (E)- and (Z)-3-p-methoxyphenyl-3-phenyl-acrylic acid.

Step 3.

The procedure of Step 3 of Example 1 was repeated except that 3-p-methoxyphenyl-3-phenyl-acrylic acid (254.5 mg, 1 mmol) was used instead of 3,3-diphenyl-acrylic acid to react with 9,10-phenanthrene quinone (44 mg, 0.21 mmol) and triphenyl arsen oxide (5 mg). Work-up gave 23.5 mg desired photochromic oxazine as yellow crystal (yield: 5.66%).

$^1$HNMR (CDCl$_3$): δ3.74 (s, 3H), 6.84 (d, 2H, J=8.7 Hz), 7.29–7.42 (m, 5H), 7.50–7.60 (m, 3H), 7.61–7.66 (m, 3H), 8.07 (s, 1H), 8.42–8.62 (m, 4H).

$^{13}$CNMR (CDCl$_3$): δ55.2, 79.4, 114.0, 122.5, 122.7, 122.8, 122.8, 122.9, 125.1, 125.2, 126.8, 126.9, 127.0, 127.5, 128.3, 128.6, 129.8, 131.2, 133.3, 138.0, 141.6, 155.9. 159.7.

Example 4

Step 1.

A mixture of anisole (11.9 g, 0.11 mole) and p-fluorobenzoyl chloride (97%, 16.34 g, 0.1 mole) in dichloromethane (50 ml) was added aluminum chloride (14.67 g, 0.11 mole) in small portions with stirring under ice-water cooling. After addition, the reaction mixture was stirred at room temperature for 1 hour, poured into a mixture of crushed ice (400 g) and hydrochloric acid (20 ml), and stirred until the orange color discharged. The mixture was extracted with dichloromethane, dried over sodium sulfate, passed through a short silica gel column and washed with dichloromethane. Solvent was removed, the residue was re-crystallized from dichloromethane-hexane, 21.96 g colorless crystal was obtained (yield: 95.4%). $^1$HNMR showed the product to have a structure consistent with p-fluorophenyl-p-methoxyphenyl ketone.

$^1$HNMR (CDCl$_3$): δ3.89 (s, 3H), 6.97 (d, 2H, J=8.7 Hz), 7.13 (dd, 21, J=8.7 Hz), 7.76–7.84 (m, 4H).

Step 2.

The procedure of Step 1 of Example 1 was repeated except that p-fluorophenyl-p-methoxyphenyl ketone (4.60 g, 20 mmol) was used instead of benzophenone and the reaction time was 48 hours. The resulting oil contained mostly (E) and (Z)-3-p-fluorophenyl-3-p-methoxyphenyl acrylic acid ethyl ester which was used in Step 3 without further purification.

Step 3.

The oil obtained in Step 2 was hydrolyzed in a mixture of KOH (5.2 g) and methanol (30 ml) for 80 minutes, cooled, and solvent was removed in vacuo. Water (30 ml) was added, the mixture filtered with suction, and washed with water. The filtrate was extracted with ether (15 ml) and the aqueous layer was separated and acidified with 4 M hydrochloric acid until the pH was <1. The solid was collected by filtration and re-crystallized from dichloromethane/hexane, 4.8 g white crystal was obtained (yield: 88.1%). $^1$HNMR showed the recovered product to have structure consistent with a mixture of (E) and (Z) 3-p-fluorophenyl-p-methoxyphenyl-acrylic acid.

Step 3.

The procedure of Step 3 of Example 1 was repeated except that 3-p-fluorophenyl-p-methoxyphenyl-acrylic acid (272.5 mg, 1 mmol) was used instead of 3,3-diphenyl-acrylic acid to react with 9,10-phenanthrene quinone (60 mg, 28.8 mmol) and triphenyl arsen oxide (5 mg). Work-up gave 75 mg desired photochromic oxazine as yellow crystal (yield: 17.3%).

$^1$HNMR (CDCl$_3$): δ3.74 (s, 3H), 6.85 (m, 2H), 7.04 (m, 2H), 7.38 (m, 2H), 7.46–7.60 (m, 3H), 7.62–7.70 (m, 3H), 8.02 (s, 1H), 8.43–8.47 (m, 1H), 8.54–8.63 (m, 3H).

$^{13}$CNMR (CDCl$_3$): δ55.2, 79.0, 114.0, 115.3, 115.6, 115.6, 122.6, 122.7, 122.8, 125.0, 125.0, 125.1, 126.8, 127.3, 127.6, 128.4, 128.8, 128.9, 129.5, 131.1, 132.8, 137.2, 137.2, 137.7, 155.4, 159.6, 164.1.

Example 5

Step 1.

To a stirred suspension of sodium hydride (0.48 g, 20 mmol) in dry THF (20 ml) was added dropwise a solution of triethyl phosphonoaetate (4.48 g, 20 mmol) in dry THF (25 ml) under nitrogen with ice-water bath cooling. After 40 minutes, the solution was transferred to a dropping funnel, added dropwise to a refluxing solution of bis (p-methoxyphenyl) ketone in dry THF (20 ml) over 20 minutes. The reaction mixture was refluxed for 48 hours and was then hydrolyzed with a saturated sodium chloride solution (40 ml). The aqueous phase was extracted with ether (3×70 ml). The combined organic extracts were dried, filtered and concentrated to afford a residue which was purified by chromatography eluting with methylenechloride/ hexane (1:2). Colorless oil (4.23 g) was obtained (yield: 67.8%). $^1$HNMR showed that the recovered product to have structure consistent with 3,3-bis(p-methoxyphenyl)-acrylic acid ethyl ester $^1$HNMR (CDCl$_3$): δ1.16 (t, 3H, J=7.1 Hz), 3.81 (s, 3H), 3.84 (s, 3H), 4.07 (q, 2H J=7.1 Hz), 6.22 (s, 1H), 6.84 (d, 2H, J=9.1 Hz), 6.90 (d, 2H, J=9.1 Hz), 7.15 (d, 2H, J=9.1 Hz), 7.24 (d, 2H, J=9.1 Hz).

Step 2.

The 3,3-bis(p-methoxyphenyl)-acrylic acid ethyl ester (4.23 g, 13.5 mmol) obtained in Step 1 was hydrolyzed in 22 ml methanol in the presence of potassium hydroxide (3.7 g, 66 mmol) for 1 hour under reflux. The cooled reaction mixture was poured into ice-water (50 ml), acidified with dilute hydrochloric acid until the pH was <1. The resulted solid was filtered, washed with water and re-crystallized from ethylacetate/hexane. White solid (3.6 g) was obtained (yield: 93.78%). $^1$HNMR showed the recovered product to have a structure consistent with 3,3-bis(p-methoxyphenyl)- acrylic acid.

$^1$HNMR (CDCl$_3$): δ3.82 (s, 3H), 3.85 (s, 3H), 6.22 (s, 1H), 6.85 (d, 2H, J=9.0 Hz), 6.91 (d, 2H, J=8.7 Hz), 7.17 (d, 2H, J=8.7 Hz), 7.24 (d, 2H, J=8.7 Hz).

Step 3.

The procedure of Step 3 of Example 1 was repeated except that 3,3-bis(p-methoxyphenyl)-acrylic acid (284.3 mg, 1 mmol) was used instead of 3,3-diphenyl-acrylic acid to react with 9,10-phenanthrene quinone (43 mg, 0.2 mmol) and triphenyl arsen oxide (5 mg). Work-up gave 8 mg desired photochromic oxazine as yellow crystal (yield: 1.8%).

$^1$HNMR (CDCl$_3$): δ3.75 (s, 6H), 6.85 (d, 2H, J=8.7 Hz), 7.41 (d, 2H, J=9.1 Hz), 7.52–7.60 (m, 1H), 7.62–7.68 (m, 3H), 8.03 (s, 1H), 8.43–8.47 (m, 1H), 8.54–8.63 (m, 3H).

$^{13}$CNMR (CDCl$_3$): δ55.2, 79.3, 113.0, 122.5, 122.7, 122.8, 122.9, 125.1, 126.8, 127.3, 127.5, 128.5, 129.8, 131.2, 133.5, 156.1. 159.7.

Example 6

The oxazine compounds produced in Examples 1, 3, 4, and 5 were dissolved in organic solvent, then exposed to UV irradiation at 365 nm for 15 seconds. The solutions each developed an intense coloration and then lost the color once the UV radiation was discontinued. The maximum absorption in the visible regions are given in the Table below. The typical absorption has two bands. A strong absorption around 450–490 nm depends on the structure of photo- chrome and solvent, together with a weaker absorption at longer wavelength which is approximately 100 nm longer.

TABLE 1

| | $\lambda_{max}$ (nm) | | | | |
|---|---|---|---|---|---|
| | Hexane | Toluene | Dioxane | Acetonitrile | Methanol |
| 1 | 451 | 456 | 447 | 444 | 448 |
| 3 | 474 | 478 | 469 | 466 | 471 |
| 4 | 473 | 478 | 468 | 465 | 470 |
| 5 | 487 | 493 | 486 | 483 | 487 |

We claim:

1. A compound comprising the formula:

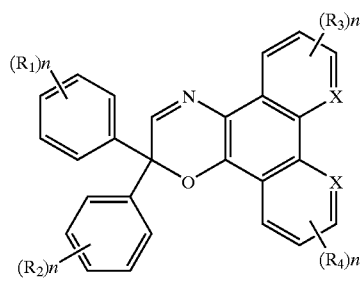

wherein X is nitrogen or carbon; $R_1$, $R_2$, $R_3$, and $R_4$ are each independently hydrogen, hydroxy, halogen, benzyl, formyl, nitro, cyano, aryl, aryl ($C_1$–$C_4$) alkyl, aryloxy, cyclo ($C_3$–$C_6$) alkyl, ($C_1$–$C_{18}$)alkoxy, halo ($C_1$–$C_6$)alkoxy, ($C_1$–$C_4$) alkoxycarbonyl or a heterocyclic nitrogen-containing substituent having 5 or 6 atoms in the ring; and n=1 or 2.

2. The compound of claim 1, wherein X is carbon or nitrogen; $R_1$, $R_2$, $R_3$, and $R_4$ are each independently hydrogen, hydroxy, fluoro, chloro, bromo, benzyl, formyl, nitro, cyano, aryl, aryl ($C_1$–$C_4$)alkyl, aryloxy, cyclo ($C_3$–$C_6$) alkyl, ($C_1$–$C_4$)alkoxy, ($C_1$–$C_4$)alkoxycarbonyl, or a heterocyclic nitrogen-containing substituent having 5 or 6 atoms in the ring; and n=1 or 2.

3. The compound of claims 1 or 2, wherein the heterocyclic nitrogen-containing substituent is pyrrolidino, piperidine, or morpholino.

4. The compound of claim 2, wherein X is carbon or nitrogen, $R_1$, $R_2$, $R_3$, and $R_4$ are each independently hydrogen, fluoro, chloro, methyl, methoxy, ethoxy, methoxycarbonyl, ethoxycarbonyl, piperidino, morpholino, or pyrrolidino.

5. A compound selected from the group consisting of 2,2-diphenyl-phenanthro (9,10)-2H-[1,4]-oxazine, 2-(4- methoxyphenyl)-2-phenyl-phenanthro (9,10)-2H-[1,4]- oxazine, 2-(4-fluorophenyl)-2-(4-methoxyphenyl)- phenanthro (9,10)-2H-[1,4]-oxazine, and 2,2-Bis(4- methoxyphenyl)-phenanthro (9,10)-2H-[1,4]-oxazine.

6. A process for producing a photochromic compound, comprising the step of:

heating an isocyanate derivative of the formula:

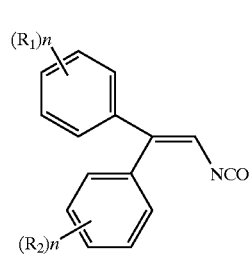

IX with a symmetric quinone of the formula:

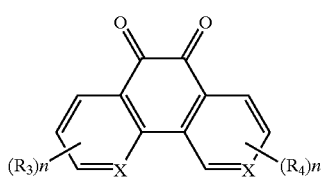

X wherein in each formula X is nitrogen or carbon $R_1$, $R_2$, $R_3$ and $R_4$ are each independently hydrogen, hydroxy, halogen, benzyl, formyl, trifluoromethyl, nitro, cyano, aryl, aryl ($C_1$–$C_4$)alkyl, aryloxy, cyclo ($C_3$–$C_6$)alkyl, ($C_1$–$C_{18}$)alkoxy, halo ($C_1$–$C_6$)alkoxy, ($C_1$–$C_4$)alkoxycarbonyl or a heterocyclic nitrogen-containing substituent having 5 or 6 atoms in the ring; and n=1 or 2 and wherein the heating is carried out in the presence of a catalytic amount of a triphenyl arsen oxide.

7. The process of claim 6, wherein the quinone is substituted or unsubstituted 9,10 -phenanthrene-9,10-dione, or substituted or unsubstituted 9,10-1,10-phenanthroline-5,6-dione.

8. The process of claim 6, wherein the heating is carried out at a temperature of about 40° C. to about 120° C. for about 2 to about 24 hours.

9. A process for producing a photochromic compound, comprising heating an aza-ylide compound of the formula XIV:

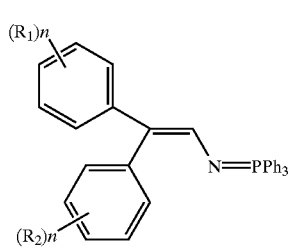

XIV with a symmetrical quinone of the compound:

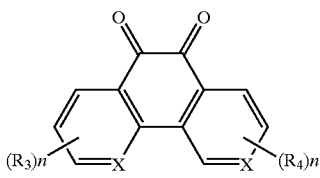

X wherein in each formula X is nitrogen or carbon; $R_1$, $R_2$, $R_3$ and $R_1$ are each independently hydrogen, hydroxy, halogen, benzyl, formyl, trifluoromethyl, nitro, cyano, aryl, aryl ($C_1$–$C_4$)alkyl, aryloxy, cyclo ($C_3$–$C_6$)alkyl, ($C_1$–$C_{18}$)alkoxy, halo ($C_1$–$C_6$)alkoxy, ($C_1$–$C_4$)alkoxycarbonyl or a heterocyclic nitrogen-containing substituent having 5 or 6 atoms in the ring; and n=1 or 2.

10. The process of claim 9, wherein the quinone is substituted or unsubstituted 9,10-phenanthrene-9,10-dione or substituted or unsubstituted 9,10-1,10-phenanthroline-5,6-dione.

11. The process of claim 9, wherein reaction is carried out at a temperature of about 60° C. to about 120° C. for about 4 to about 24 hours.

* * * * *

UNITED STATES PATENT AND TRADEMARK OFFICE
CERTIFICATE OF CORRECTION

PATENT NO. : 6,686,466 B2  Page 1 of 1
DATED : February 3, 2004
INVENTOR(S) : Weili Zhao and Erick M. Carreira It is certified that error appears in the above-identified patent and that said Letters Patent is hereby corrected as shown below:

<u>Column 14,</u>
Line 28, replace "$R_1$" with -- $R_4$ --

Signed and Sealed this

Twentieth Day of April, 2004

JON W. DUDAS
*Acting Director of the United States Patent and Trademark Office*